United States Patent
Bonnet et al.

(10) Patent No.: US 10,335,291 B2
(45) Date of Patent: Jul. 2, 2019

(54) HYDRAULIC SYSTEM FOR A KNEE-ANKLE ASSEMBLY CONTROLLED BY A MICROPROCESSOR

(71) Applicant: PROTEOR, Saint-Apollinaire (FR)

(72) Inventors: Xavier Bonnet, Dijon (FR); Francis Djian, Genlis (FR)

(73) Assignee: PROTEOR, Saint-Apollinaire (FR)

(*) Notice: Subject to any disclaimer, the term of this patent is extended or adjusted under 35 U.S.C. 154(b) by 0 days.

(21) Appl. No.: 14/417,085

(22) PCT Filed: Jul. 26, 2013

(86) PCT No.: PCT/EP2013/065845
§ 371 (c)(1),
(2) Date: Jan. 23, 2015

(87) PCT Pub. No.: WO2014/016424
PCT Pub. Date: Jan. 30, 2014

(65) Prior Publication Data
US 2015/0182354 A1 Jul. 2, 2015

(30) Foreign Application Priority Data

Jul. 27, 2012 (EP) .................. 12305924

(51) Int. Cl.
*A61F 2/64* (2006.01)
*A61F 2/66* (2006.01)
(Continued)

(52) U.S. Cl.
CPC .............. *A61F 2/64* (2013.01); *A61F 2/6607* (2013.01); *A61F 2/68* (2013.01); *A61F 2/66* (2013.01);
(Continued)

(58) Field of Classification Search
CPC .. A61F 2/64; A61F 2/6607; A61F 2/66; A61F 2/68; A61F 2002/745
See application file for complete search history.

(56) References Cited

U.S. PATENT DOCUMENTS 2,478,721 A    8/1949   Stewart
2,537,351 A * 1/1951   Johnson .................. A61F 2/604
                                                   623/26
(Continued)

FOREIGN PATENT DOCUMENTS

EP      0 549 855 A2    7/1993
WO     96/41599 A1    12/1996
(Continued)

OTHER PUBLICATIONS

Hemmerich et al., "Hip, Knee, and Ankle Kinematics of High Range of Motion," Journal of Orthopaedic Research, Apr. 2006, pp. 770-781.

*Primary Examiner* — Bruce E Snow
*Assistant Examiner* — Melissa A Hoban
(74) *Attorney, Agent, or Firm* — Seed IP Law Group LLP (57) ABSTRACT

A prosthesis can include a femoral segment suitable for a femoral connection to a user and a tibial segment connected to the femoral segment based on an articulation which reproduces movements of the knee, the tibial segment being articulated on a foot segment based on an articulation reproducing movements of the ankle, a first hydraulic damper the ends of which are joined respectively with the femoral and tibial segments, and a second hydraulic damper of which the ends are joined respectively with the tibial and foot segments.

16 Claims, 8 Drawing Sheets

(51) Int. Cl.
*A61F 2/68* (2006.01)
*A61F 2/70* (2006.01)
*A61F 2/74* (2006.01)
*A61F 2/76* (2006.01)

(52) U.S. Cl.
CPC ... *A61F 2002/704* (2013.01); *A61F 2002/745* (2013.01); *A61F 2002/748* (2013.01); *A61F 2002/764* (2013.01); *A61F 2002/7625* (2013.01); *A61F 2002/7635* (2013.01)

(56) References Cited

U.S. PATENT DOCUMENTS

| | | | |
|---|---|---|---|
| 4,662,486 A * | 5/1987 | Stenberg | A61F 2/64 16/56 |
| 5,092,902 A * | 3/1992 | Adams | A61F 2/64 623/26 |
| 6,443,993 B1 | 9/2002 | Koniuk | |
| 6,673,117 B1 * | 1/2004 | Soss | A61F 2/64 623/24 |
| 8,623,098 B2 * | 1/2014 | Goldfarb | A61F 2/60 623/25 |
| 9,132,023 B2 * | 9/2015 | Moser | A61F 2/6607 |
| 2004/0111163 A1 | 6/2004 | Bedard et al. | |
| 2005/0197717 A1 | 9/2005 | Ragnarsdottir et al. | |
| 2005/0258009 A1 * | 11/2005 | Reinhardt | A61F 2/68 188/266.5 |
| 2005/0283257 A1 | 12/2005 | Bisbee, III et al. | |
| 2006/0122711 A1 | 6/2006 | Bedard et al. | |
| 2007/0050047 A1 | 3/2007 | Ragnarsdottir et al. | |
| 2008/0287850 A1 * | 11/2008 | Adarraga | A61F 5/0102 602/26 |
| 2009/0192619 A1 * | 7/2009 | Martin | A61F 2/60 623/18.11 |
| 2009/0299489 A1 * | 12/2009 | Gramnaes | A61F 2/64 623/27 |
| 2010/0241242 A1 | 9/2010 | Herr et al. | |
| 2010/0312363 A1 * | 12/2010 | Herr | A61F 2/64 623/39 |
| 2011/0098828 A1 | 4/2011 | Balboni et al. | |
| 2011/0160871 A1 * | 6/2011 | Boone | A61F 2/60 623/26 |
| 2011/0166489 A1 | 7/2011 | Angold et al. | |
| 2013/0204395 A1 * | 8/2013 | Gramnaes | A61F 2/64 623/26 |
| 2014/0128993 A1 * | 5/2014 | Shen | A61F 2/68 623/44 |
| 2014/0222167 A1 * | 8/2014 | Poulson, III | A61F 2/6607 623/52 |
| 2014/0371874 A1 * | 12/2014 | Wu | A61F 2/80 623/47 |
| 2014/0379096 A1 * | 12/2014 | Zahedi | A61F 2/66 623/25 |

FOREIGN PATENT DOCUMENTS

| | | |
|---|---|---|
| WO | 2005/087144 A2 | 9/2005 |
| WO | 2008/103917 A1 | 8/2008 |

* cited by examiner

HYDRAULIC SYSTEM FOR A KNEE-ANKLE ASSEMBLY CONTROLLED BY A MICROPROCESSOR

BACKGROUND

Technical Field

The present invention pertains to a knee-ankle prosthesis for lower-limb amputees and in particular to a hydraulic system for the articulation of the knee and ankle controlled by a microprocessor.

Description of the Related Art

It is common knowledge that prostheses for femoral amputees generally consist of a prosthetic knee and a foot-ankle assembly. There are multiple types of prosthetic knees; however, there are two broad distinct categories: passive knees and active knees.

Passive mechatronic knees are controlled by microprocessors, and are referred to as passive since they do not provide energy but rather use the energy derived from walking. They contain a hydraulic or magnetorheological damper that controls the flexion and extension movements of the knee, through the use of one or several solenoid valves, of which the flow is managed by a microprocessor. The braking action of the damper is strong in the stance phase in order to avoid falling and weak during the swing phase to guide the pendular motion of the leg.

As for active knees, they include a motor that provides energy in addition to the energy derived from walking.

All these knees contain several sensors that allow determining the timing of changing the positions of the solenoid valves or changing the motor torque. The sensors allow the recognition of the exact point in the walking movements at which the leg is currently in, such as the stance phase or swing phase for example, and they also allow measuring the walking speed.

The latest prosthetics are based on the recognition of the situation in which the amputee is (slope, stairs, seated, etc.) such as the Genium® (passive knee marketed by Otto Bock) and the POWER KNEE® (active knee marketed by Össur-Victhom) which has been described in particular in the U.S. patent applications US 2004/0111163 and US 2006/0122711. Situation recognition requires using a large number of sensors and more elaborate recognition algorithms. Recognizing these situations allows adapting the flexion and extension resistance setting as per the situation encountered by the person wearing the prosthetic.

The C-Leg®, marketed by Otto Bock, is particularly well-known, and is historically the first passive knee with hydraulic dampers controlled by microprocessors in the stance and swing phase. This knee has been described in particular in the international patent application WO 96/41599 and in the European patent application EP549855. It controls the flexion and extension for the entire walking cycle (in stance phase and swing phase). Recently, Otto Bock has launched the Genium® knee, which is a significant step forward over the C-Leg. This knee is still a passive knee, but contains numerous improvements related to the recognition of complex situations such as climbing stairs, slopes, seated position, etc.

Another well-known knee is the RHEO KNEE®, marketed by Össur, which is a magnetorheological damper based passive knee. This knee has been described in particular in the U.S. patent application US 2005/0283257 and international patent application WO 2005/087144.

Analytical studies of the movements have shown that while descending stairs, the braking torque of the C-Leg® prosthetic knee remains lower than the braking torque of the contralateral limb. This results in a "fall" on the contralateral limb and a significant increase in the effort taken by it. This effort results in an increase in the joint torques in the entire contralateral limb. Moreover, in order to descend stairs with a "conventional" knee, the prosthetic foot must be placed on the ground on the nose of the step in order to allow the foot to roll and the tibia to advance. This placement must be precise, which requires extra attention from the user. Persons wearing prosthetics thus avoid descending stairs in alternating steps if the stairs are too rough or if the floor is too slippery, etc.

There are also foot-ankle prosthesis which can be classified into the following three categories: purely passive ankles, passive mechatronic ankles with solenoid valves and active mechatronic ankles Purely passive ankles include neither sensors nor solenoid valves nor any machines. Passive ankles with solenoid valves allow controlling the hydraulic dampening action and the mechatronic ankles have sensors, solenoid valves or a motor.

The PROPRIO FOOT® foot-ankle, marketed by Össur and disclosed particularly in the U.S. patent applications US 2005/0197717 and US 20070050047, is a mechatronic prosthesis of which the ankle consists of an electrical motor controller by sensors. Such an arrangement allows relieving the end of the foot during the swing phase to avoid it from damaging the floor; it also allows modifying the heel height setting (if the user is changing shoes), adapting the angle of the ankle in the stance phase depending on the slope and while using stairs, this adaptation always takes place when the user's weight is off the ankle, in the pendular phase, and modifying the ankle angle when in seated position and when transitioning from seated to standing position and vice-versa.

It will be noted that, even though the motor works only during the swing phase, it is already very large, noisy and consumes a lot of energy since it is the motor that allows moving the leg in the swing phase in each step. The ProprioFoot® forces the user to carry a large battery around and to recharge it every day. Moreover, the motor is likely to be noisy.

There is another foot-ankle, the Echelon®, marketed by Endolite and described in particular in the international patent claim WO2008103917, which is a purely passive ankle that consists of a small linear hydraulic damper which allows a mobility of 3° in dorsiflexion (direction of rotation of the foot in which the big toe is raised upwards) and 6° in plantiflexion (direction of rotation of the foot in which the big toe is pushed downwards). Two valves with manually adjustable tips allow adjusting the flow of dorsiflexion and plantiflexion separately. The plantiflexion is particularly important for descending stairs, which allows quickly placing the flat of the foot on the ground.

However, mobility in dorsiflexion is limited)(3°). This compromise allows satisfactory walking on flat surfaces and while climbing up a slope.

Moreover, the Elan® is a passive mechatronic ankle, which is a developed version of the Echelon® foot-ankle that consisted of manual dorsiflexion and plantiflexion valves that have been replaced by solenoid valves. This allows adjusting the hydraulic dampening depending on the slope and walking speed, and the amounts of mobility in dorsiflexion and plantiflexion have not been modified. This solution allows modifying the hydraulic resistances only when a change in slope is detected, i.e., less frequently, which lowers the battery consumption. It is possible to increase the amount of the dorsiflexion while climbing and the amount of plantiflexion when descending. However, such a solution appears to be limited owing to reasons of space requirement.

There is also the Motion Foot foot-ankle, marketed by Fillauer, which is a purely passive ankle with a functioning similar to that of the Echelon®, the only difference being that the hydraulic cylinder is rotary and not linear, as well as the Raize® foot-ankle, marketed by Fillauer and described in the U.S. Pat. No. 6,443,993 in particular, which is a mechatronic passive ankle that consists of a linear hydraulic damper controlled by a valve, which in turn is controlled by microprocessors and sensors. The valve is adjusted continuously and allows controlling the resistance and amplitude of the dorsiflexion as well as the resistance of the plantiflexion. The functions executed are thus more important than the Elan®, marketed by Endolite, but the valve is continuously controlled, which consumes a high amount of energy.

In the same manner as the Echelon® marketed by Endolite, the Raize™ does not move in the swing phase.

None of these ankles (Echelon®, Elan®, Raize™) thus allow increasing the distance from the big toe to the floor during the swing phase. The person wearing the prosthesis will increase this distance by lifting his pelvis from the side of the prosthesis during the swing phase. This strategy expends a lot of energy (elevation of the center of mass) and results in twisting of the pelvis and the lower back.

Lastly, there are many knee-ankles such as the Hydracadence, which is described in particular in the U.S. Pat. No. 2,478,721, which is a knee-ankle assembly that contains a hydraulic damper that controls the angle of the knee, and another hydraulic damper that manages the angle of the ankle There is a hydraulic connection between these 2 cylinders which allows coordination between the angle of the ankle and the angle of the knee. The function carried out by this knee is flexion of the ankle during the pendular phase, which allows avoiding damaging the bottom of the foot against the floor and this dorsiflexion in the swing phase being a result of the flexion of the knee, adjusting the dorsiflexion stopper allows adjusting the prosthesis as per the change in footwear (heel height), and free plantiflexion that facilitates the heel strike.

This knee-ankle consists of one valve that controls the adjustment of the dampening of the knee in the pendular phase. Moreover, this prosthesis, which was designed in the 1940s, does not include any mechatronics and thus cannot adapt to different walking situations.

BRIEF SUMMARY

One of the purposes of the invention is to thus provide a solution for these disadvantages by offering a knee-ankle prosthesis of a simple and non-cumbersome design, which will allow reproducing the movements made by bi-articular muscles such as the gastrocnemius.

To this end and in compliance with the invention, we propose a femoral knee-ankle prosthesis intended for persons who are lower-limb amputees but still have a segment suitable for a femoral connection and a tibial segment connected to the femoral segment based on an articulation that reproduces the movements of the knee, the said tibial segment being articulated on one foot based on an articulation reproducing the movements of the ankle, an initial damper of which the ends are joined respectively with the femoral and tibial segments, and another hydraulic damper of which the ends are joined respectively with the tibial and foot segment; the said prosthesis is remarkable in that the chamber of the first hydraulic damper is connected to the chamber of the second hydraulic damper and in that it consists of the means of controlling the first and/or second hydraulic damper depending on the phase of the walking cycle such as the stance phase or the swing phase and/or real-life situations such as stairs, slopes or standing position, etc., in such a manner that the flexion of the knee allows the dorsiflexion of the ankle in proportion to the movement of the knee during the stance phase and such that the flexion of the knee results in the dorsiflexion of the ankle during the swing phase.

As per an initial variant of execution, the chamber of the first hydraulic damper is connected to the chamber of the second hydraulic damper through a conduit fitted with an on-off valve that is controlled through a control unit.

As per a second variant of execution, the chamber of the first hydraulic damper is connected to the chamber of the second hydraulic damper through a conduit connected laterally to the chamber of the first hydraulic damper, the said first hydraulic damper and/or second hydraulic damper being controlled through a control unit.

The movements of the dampers are regulated by one or several proportional valves.

The said proportional valves are controlled through the control unit depending on the phase of the walking cycle and the situation faced by the person.

The said phase of the walking cycle and/or situation are determined by the control unit based on the data obtained from the sensors placed on the knee and/or ankle joint.

Moreover, each sensor consists of a kinetic, kinematic or inertial sensor.

In addition to this, the control unit controls the valve of the conduit and/or valves for the regulation of the damper in such a manner as to ensure that the flexion/extension resistances of the knee and/or ankle joint are varied.

The flexion of the knee allows a dorsiflexion of the ankle in proportion to the movement of the knee during the stance phase and the flexion of the knee results in dorsiflexion of the ankle during the swing phase.

The connection between the flexion of the knee and the dorsiflexion of the ankle is between 1/4 and 2/5 and the connection between the flexion of the knee and the dorsiflexion of the ankle is more or less 1/3.

Preferably, the control unit contains at least one microprocessor.

Moreover, the said means of controlling include an algorithm that determines the moment of articulation depending on an angle of the segment adjacent to the articulation compared to a reference and/or the angular speed of the segment adjacent to the articulation in a determined reference and an algorithm that determines the controlling instructions for the drive means depending on the ratio between the moment the articulation force is applied and an angle of a segment adjacent to the articulation compared to a reference.

This bi-articular control (knee-ankle) is of crucial importance for all triple flexion movements (flexion/extension of the hip, knee and ankle) such as the transition from standing and seated position, descending stairs with the foot flat on the stair, squat movements, etc. The invention allows a lower-limb amputee to carry out these triple flexion movements and control them using the remaining part of their limb (hip).

This bi-articular control is adapted by the microprocessor depending on the phase of the walking cycle (stance/swing) and depending on the situation in which the person is (stairs, slope, etc.).

BRIEF DESCRIPTION OF THE SEVERAL VIEWS OF THE FIGURES

Other advantages and characteristics can be explained better through the following description of several variants of execution, given as non-exhaustive examples, of the femoral knee-ankle prosthesis in compliance with this invention, in reference to the diagrams in the annex on which.

DETAILED DESCRIPTION

In order to make things clearer, in the following description, the same elements have been referred to by the same references in the various figures. Moreover, the various cross sections are not drawn to scale.

Figures 1, 2:
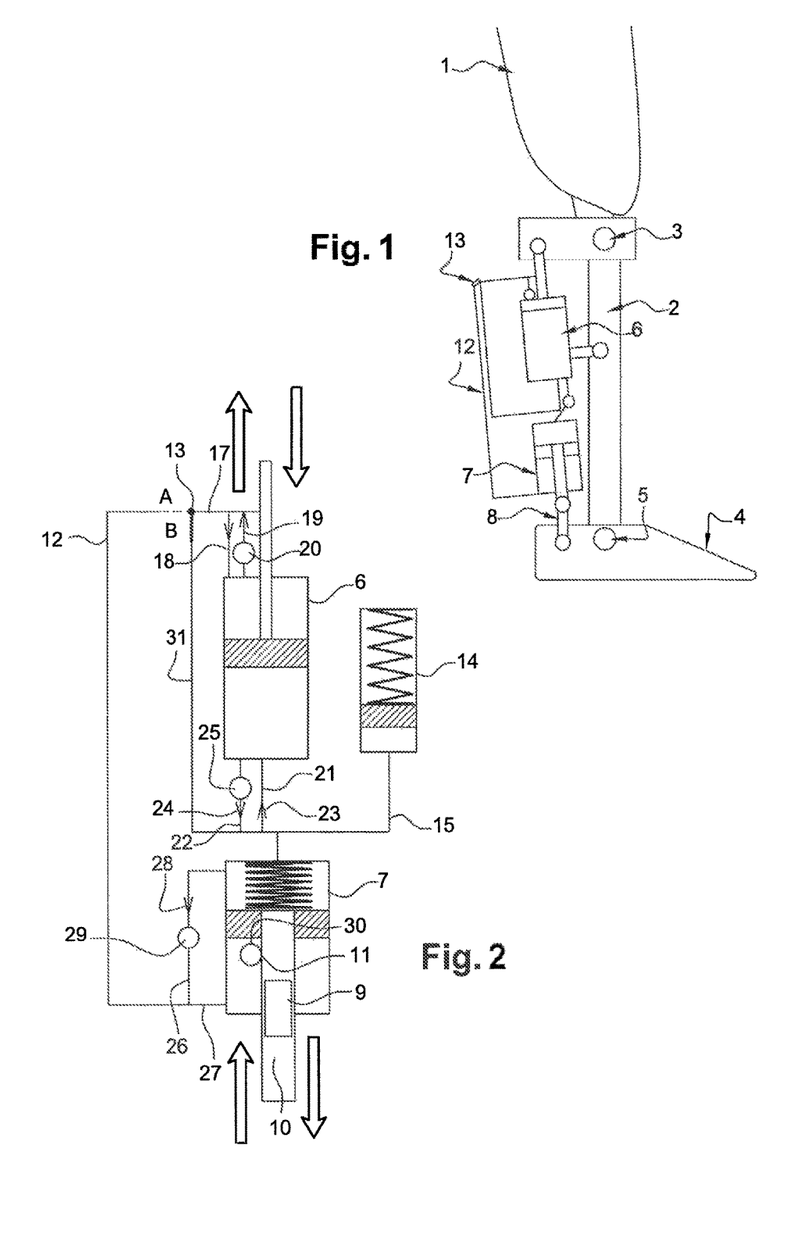
FIG. 1 is a representation of the femoral knee-ankle prosthesis in compliance with the invention.
FIG. 2 is a schematic representation of the hydraulic system of the prosthesis in compliance with the invention.

With reference to FIG. 1, the femoral knee-ankle prosthesis, in compliance with the invention, includes a femoral segment (1) that is suitable for a femoral connection, and a tibial segment (2) connected to the femoral segment (1) based on articulation (3) reproducing the movements of the knee, the said tibial segment (2) being articulated to a foot (4) based on an articulation (5) reproducing the movements of the ankle. The prosthesis consists of a dual purpose hydraulic damper (6) the ends of which are connected respectively to the femoral segment (1) and the tibial segment (2), and a second dual purpose hydraulic damper (7) the ends of which are connected respectively to the tibial segment (2) and the foot (4) using a connecting rod (8).

With reference to FIGS. 1 and 2, the second hydraulic damper (7) has a slide valve (9) that is slide mounted in the hollow shaft (10) of the second damper (7), and the said hollow shaft (10) includes at least one slot (11) that allows communication between the two chambers of the damper (7), depending on the position of the said slot (9) in the hollow shaft. The upper chamber of the first hydraulic damper (6) is connected to the lower chamber of the second hydraulic damper (7) using a conduit (12) fitted with an on-off valve (13) that is controlled by a microprocessor, not given in the figures, depending on the walking phase such as the stance phase or the swing phase and/or the situation such as descending stairs, a slope or just standing and similar position, as explained in detail further below. It must be noted that the microprocessor also controls the slide valve (9) depending on the walking phase such as the stance phase or the swing phase and/or the situation such as descending stairs, a slope or just standing and similar position.

It is evident that the microprocessor can be substituted by any equivalent control unit commonly known in the trade such as a micro-controller, and still be compliant with the scope of the invention.

The chambers of the first and second dampers (6,7) are connected to a hydraulic collector (14) through a conduit (15) which is also connected to one of the channels of the on-off valve (13). A second channel of the on-off valve (13) is connected to two conduits (16) and (17) which are connected to the first chamber of the first hydraulic damper (6). The first conduit (16) contains a check valve (18) and the second conduit (17) contains a check valve (19) and a solenoid valve (20) which controls the extension of the knee. The second chamber of the first damper (6) is connected to the conduit (15) by two conduits (21) and (22), the first conduit (21) contains a check valve (23) and the second conduit (22) contains a check valve (24) and a solenoid valve (25) which controls the flexion of the knee. The conduit (12) is connected to the two chambers of the second hydraulic damper (7) by two connections (26) and (27), the connection (26) contains a check valve and a solenoid valve (29) which controls the plantiflexion of the ankle Lastly, the hollow shaft (10) of the second damper (7) has a slot or slots (11) which allow communication between the two damper chambers (7), depending on the position of the said slide valve (9) in the hollow shaft (10), and fitted with a solenoid valve (30) which controls the dorsiflexion of the ankle. The conduit (15) is connected to one of the channels of the on-off valve (13) via a conduit (31).

It is evident that the hollow shaft (10) of the second damper (7) can include several slots (11) and still be compliant with the invention. Moreover, the number and diameter of the slots (11) can be easily determined by an expert.

When the on-off valve (13) is in position A, during flexion, the oil arriving in the upper chamber of the first damper (6) has to pass through the conduit (12) via the second conduit (18) from the lower chamber of the second damper (7). In the swing phase, this results in the dorsiflexion of the ankle. In the stance phase, the dorsiflexion movement is allowed, but it is executed depending on the feedback of the pressures exerted on the piston of the second damper (7), and the oil may be conveyed through the regulating mechanisms during plantiflexion and dorsiflexion, i.e., solenoid valve (29) and solenoid valve (30) respectively.

When extending the knee, the oil exiting the upper chamber of the first damper (6) goes through the conduit (12) via check valves (18) and (19) up to the lower chamber of the second damper (7). In the swing phase, this causes an automatic return of the ankle in plantiflexion. In the stance phase, the movement is allowed or restricted depending on the position of the piston of the second damper (7) compared to the slide valve (9).

When the on-off valve (13) is in position B, the oil exiting and arriving in the upper chamber of the first damper (6) passes directly towards the collector (14) via the conduit (15) without passing through the second damper (7). This allows a disconnected functioning of both the dampers (6) and (7).

The solenoid valves (20,25,29,30) can be replaced by any other valve commonly known in the trade in order to regulate the movements of the dampers (6,7) and still be compliant with the scope of the invention.

The said proportional valves (20,25,29,30) are controlled by the microprocessor depending on the phase of the walking cycle and the situation faced by the person. The phase of the walking cycle and/or situation are determined by the microprocessor based on the data received from the sensors, not represented on the figures, placed on the knee and/or ankle joint. Each sensor consists of a kinetic, kinematic or inertial sensor or any other equivalent sensor commonly known in the trade such as a gyroscope or accelerometer for example. The said microprocessor controls the on-off valve (13) of the conduit and (12) the proportional valves (20,25, 29,30) for the regulation of the damper in such a manner as to ensure that the flexion/extension resistances of the knee and/or ankle joint are varied. The flexion of the knee allows a dorsiflexion of the ankle in proportion to the movement of the knee during the stance phase and the flexion of the knee results in dorsiflexion of the ankle during the swing phase.

It will be observed that the femoral prosthesis in compliance with the invention also includes a damper (6) of the knee and a second damper (7) of the ankle, of which the bodies are mechanically integrated and hydraulically connected. This coupling, which will be referred to as "knee-ankle synergy", consists of a sharing of hydraulic energy between the two dampers (6 and 7) in such a manner that, as per the status of the synergy, the flexion of the knee is capable of causing (pendular phase) or authorizing (stance phase) a flexion of the ankle, or vice versa. This synergy may be active or inactive depending on the walking situations. The prosthesis in compliance with the invention helps improving the aspects of weight and space owing to the sharing of mechanical systems, and allows placing sensors on the knee and the ankle in order to facilitate the recognition of walking situations by combining several sensors, allows sharing the battery, and allows controlling the position of the ankle depending on the knee and vice-versa.

The prosthesis in compliance with the invention allows, in particular, lifting the foot automatically in the swing phase without requiring the motor, exclusively because of the flexion of the knee, automatically folding the ankle when the knees are flexed, for example when sitting down, by associating the knee flexing angle and the ankle dorsiflexion angle.

It will be observed that this synergy exists naturally in the human body through bi-articular muscles such as the gastrocnemius.

For the standing-seated transition, the squat movements, ratio between the flexion of the knee and dorsiflexion of the knee and dorsiflexion of the ankle is between 1/4 and 2/5, and preferably 1/3.

The movements can be combined (in synergy) or dissociated. The synergy may be activated or deactivated by the activation of the on-off valve (12) controlled by a microprocessor-based control unit.

It is evident that the synergy can be constantly activated and still be compliant with the invention.

Figure 3:
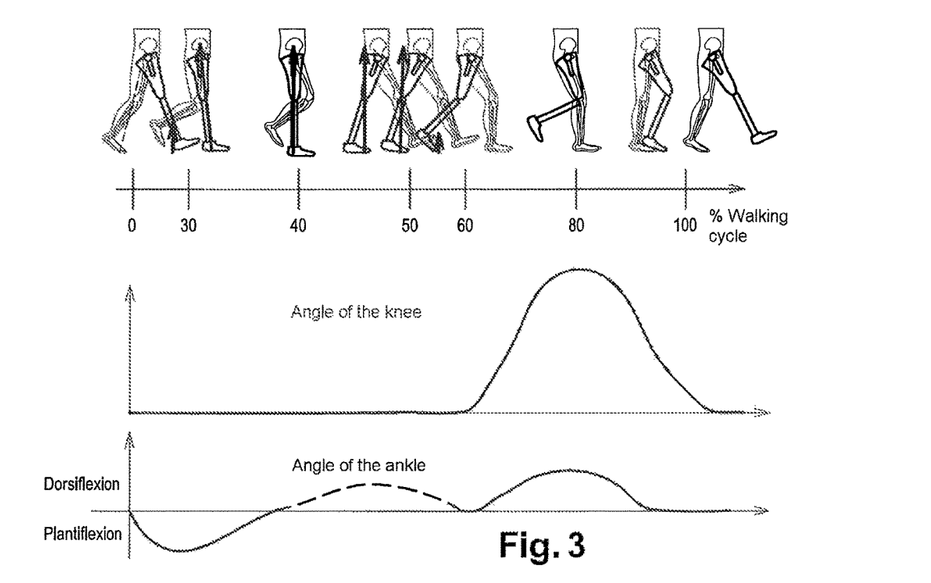
FIG. 3 is a graphical representation of the change in the angles of the knee and ankle when walking on flat surfaces, the walking cycle corresponds to the interval between two heel strikes of the same foot.

In reference to FIG. 3, walking on flat surfaces can be broken down into several parts. From 0 to 12%, the foot is quickly placed on the floor through the plantiflexion of the ankle. The flexion of the knee is controlled by a significant resistance to the flexion of the knee. From 12 to 30%, the tibia returns to the vertical position, the ankle returns to the neutral position, at the stop point of the dorsiflexion. From 30 to 48%, the knee is completely extended and the ankle is in the neutral position. The progression of the tibia is made possible through the deformation of the blade of the foot, which results in visible dorsiflexion represented by the dotted line in the figure. From 48 to 60%, the resistance to flexion of the knee is lowered to allow the initiation of the swing phase. The knee rapidly flexes to reach 30° at the end of the stance phase. The foot of the blades assumes its original, non-deformed shape. The dorsiflexion of the ankle depends on the synergy mode (see below). From 60 to 80%, the knee continues its flexion in the swing phase. The dorsiflexion of the ankle is proportional to the flexion of the knee, increasing the distance between the big toes and the floor in order to avoid risk of stumbling. From 80 to 100%, the knee once again undergoes extension, and the flexion control resistance is increased to stop the knee in case of stumbling and to prepare for the following stance phase. The behavior of the ankle depends on the mode of knee-ankle synergy.

Figure 4:
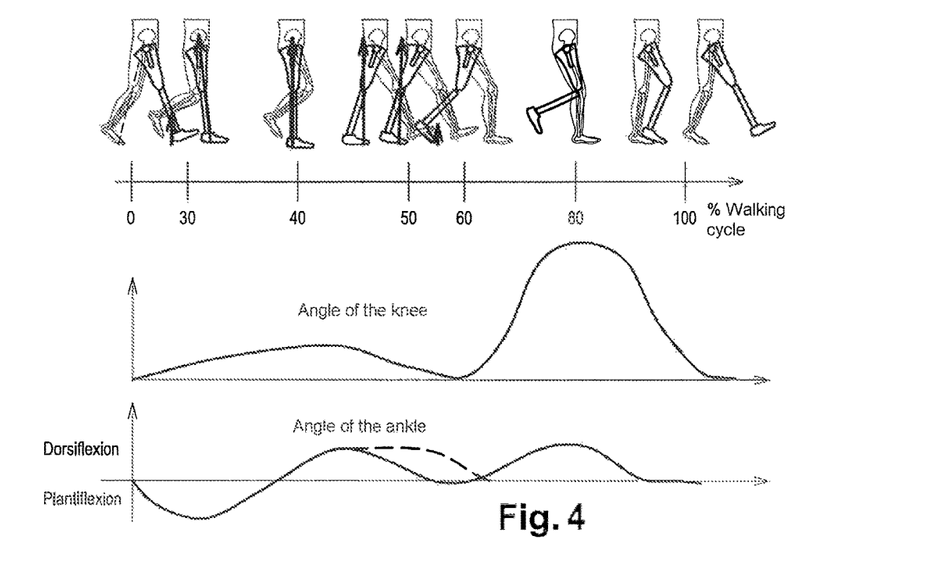
FIG. 4 is a graphical representation of the change in the angles of the knee and ankle during a walking cycle in which walking on flat surfaces includes a flexion of the knee in the stance phase called "stanceflex"

In reference to FIG. 4, walking on flat surfaces includes the flexion of the knee in stance phase, and the said flexion being commonly referred to as "stanceflex" may be broken down into several parts. From 0 to 12%, the foot is quickly placed on the floor through the plantiflexion of the ankle By changing the resistance to plantiflexion and by adjusting the resistance to flexion of the knee, the placing of the foot on a flat surface can be done through a combination of flexion of the knee and plantiflexion of the ankle From 12 to 30%, flexion of the knee allows proportional dorsiflexion of the ankle (synergy). The tibia returns to vertical position by retaining the knee flexion. From 30 to 48%, the knee is once again completely extended resulting in the ankle returning to neutral position. The energy required for stopping the knee from being extended is thus transmitted to the ankle, allowing the propulsion of the center of gravity upwards and forwards. The purpose of this is to prepare for the transition of weight to the contralateral limb.

Now, we shall explain the functioning of the prosthesis in accordance with the invention with reference to FIGS. 5A to 5F.

Figure 5A:
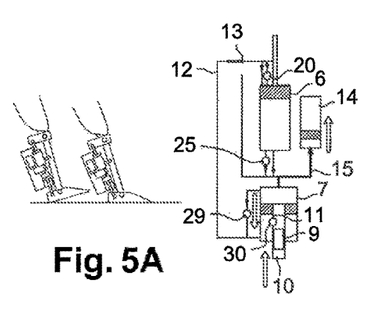
FIGS. 5A to 5F are schematic representations of the hydraulic system of the prosthesis in compliance with the invention, respectively during the heel strike and the flat placement of the foot on the floor (A), when the tibia returns to the vertical position (B), during the propulsion (C), during the initiation of the flexion of the knee (D), during the flexion of the knee in the swing phase (E) and during the return to extension of the knee (F)

With reference to FIG. 5A, during plantiflexion, i.e., from 0 to 12% of the walking cycle represented in FIG. 3, the support on the heel causes the ankle piston to move upwards. The oil from the upper chamber of the damper (7) of the ankle passes into the lower chamber via the solenoid valve (29) that regulates the plantiflexion. The extra oil is sent towards the collector (14). In order to regulate the plantiflexion, either a manual valve adjusted by the orthoprosthesist depending on the weight and walking style of the patient is used, or a solenoid valve is used to thus ensure the adaptation to situations that require a softer or harder level of dampening. This phase ends when the foot is flat on the ground or if the piston of the ankle is in the highest position.

If the on-off valve, called the synergy valve (13), is in position B, the knee does not flex and there is no "stanceflex". Contrarily, if the on-off valve, called the synergy valve (13), is open in position A, the oil can pass from the lower chamber of the foot damper (7) to the upper chamber of the knee damper (6) resulting in the flexion of the knee in stance phase (stanceflex). This flexion is controlled by regulating the flexion of the knee (significant resistance), i.e., through a solenoid valve (25).

It must be noted that the adjustment of the solenoid valves (29) and (25) more or less allows choosing the plantiflexion or "stanceflex" at the beginning of the support depending on the walking preferences of the user. If these valves (29) and (25) are controlled by the microprocessor, the plantiflexion and stanceflex are adjusted depending on the situation (slope, speed, weight bearing, etc.).

Figure 5B:
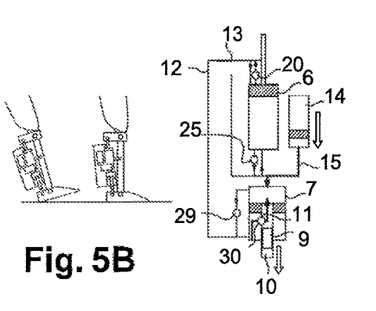

With reference to FIG. 5B, when the tibia is returning to vertical position, i.e., from 12 to 30% of the walking cycle represented on FIG. 3, once the foot is completely placed flat on the ground, the tibia returns to vertical position. The ankle returns to neutral position. The piston of the ankle is lowered. The oil passes from the lower chamber to the upper chamber through the regulation of the dorsiflexion, i.e., through the solenoid valve (30), until the openings are (11) obstructed by the slide valve (9). The ankle is in neutral position.

Figure 5C:
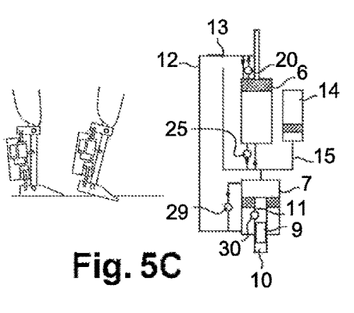

With reference to FIG. 5C, at the time of forward propulsion, i.e., from 30 to 48% of the walking cycle (end of the single foot support) represented on FIG. 3, once the tibia returns to vertical position, the ankle is locked in dorsiflexion, which allows deforming the foot of the blade to store energy. When the person is on the forefoot, the microprocessor gives instructions to modify the resistance of the knee flexion, by controlling the solenoid valve (25), at a low level. The on-off valve (13) called the synergy valve is deactivated at the same time when the knee flexion is authorized, which allows rigidifying the ankle.

Figure 5D:
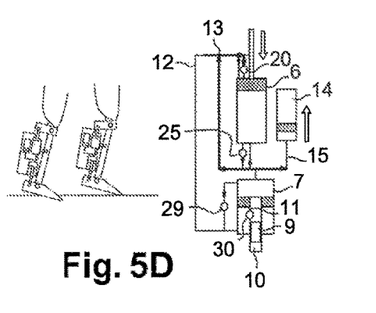
Figure 5E:
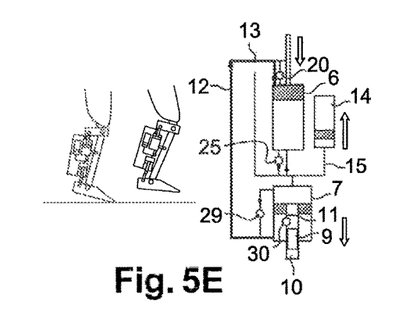

With reference to FIG. 5D, at the time of initiation of the knee flexion, i.e., from 48 to 60% of the walking cycle (second double foot support) represented on FIG. 3, the initiation of the knee flexion is then facilitated. The ankle is still blocked in order to allow restoring energy to the foot. The oil passes from the lower chamber of the damper (6) of the knee to the upper chamber and is regulated by the flexion regulation, i.e., by the solenoid valve (25). With reference to FIG. 5E, during the flexion in the swing phase, i.e., from 60 to 80% of the walking cycle represented on FIG. 3, the flexion of the knee between 30° and 60° results in the automatic dorsiflexion of the ankle with a ratio of 1/3, i.e., 10° of the ankle dorsiflexion. The ratio of 1/3 is preferred but may be between 1/4 and 2/5. The flexion regulation, i.e., the solenoid valve (25), is controlled electrically in order to be subject to the walking speed or the weight of the prosthesis (inertia of the part below the knee).

Figure 5F:
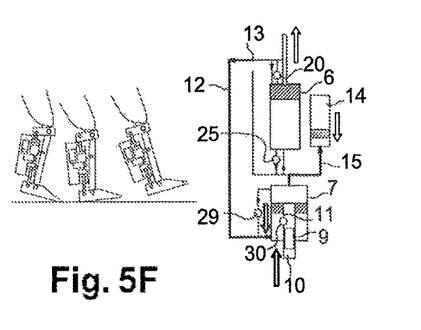

With reference to FIG. 5F, when the knee is returning to extended position in the swing phase, i.e., from 80 to 100% of the walking cycle represented on FIG. 3, once maximum flexion is reached, the knee returns to extended position. Based on the maximum flexion information, the instructions are provided by the microprocessor to block the flexion of the knee in case the person stumbles. The knee piston must be raised rapidly. This extension movement is regulated by the extension valve, i.e., the solenoid valve (20). This facilitates the passage of the fluid till approximately 5° flexion is achieved. The valve will then gradually close to dampen the terminal impact, i.e., the return of the knee to complete extended position. The on-off valve (13) called the synergy valve may either be closed to retain dorsiflexion during the return to extended position of the knee or open at the right moment when returning to extension to ensure that the foot is as far away as possible from the floor.

Figure 6:
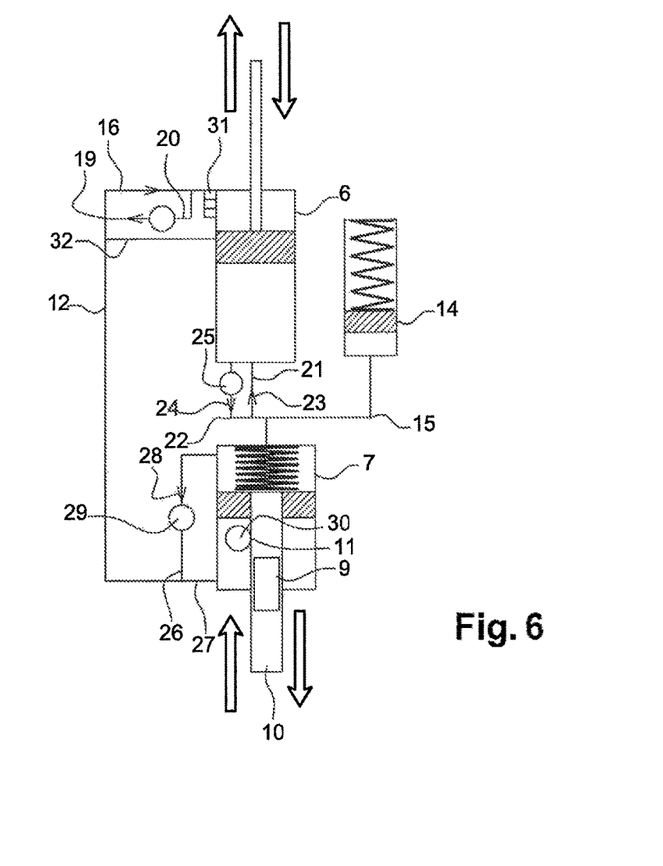
FIG. 6 is a schematic representation of a variant of execution of the hydraulic system of the prosthesis in compliance with the invention.

As per a variant of execution of the prosthesis in compliance with the invention, with reference to FIG. 6, the prosthesis, in the same manner as above, consists of a dual purpose hydraulic damper (6) the ends of which are connected respectively to the femoral segment (1) and the tibial segment (2), and a second dual purpose hydraulic damper (7) the ends of which are connected respectively to the tibial segment (2) and the foot (4). The upper chamber of the first hydraulic damper is connected to the lower chamber of the second hydraulic damper (7) through a conduit (12).

This prosthesis is different from the previous in that it does not include an on-off valve (13) controlled by the microprocessor. This on-off valve (13) and the conduit (31) connecting one of the channels of the on-off valve (13) to the conduit (15) are replaced with one or several conduits (31) connecting the chamber of the first hydraulic damper (6) to the chamber of the second hydraulic damper (7), via the solenoid valve (20) and a conduit (32) connecting the chamber of the second hydraulic damper (7), the said conduits (31, 32) being connected laterally to the chamber of the first hydraulic damper (6) and the conduit (32) opening into the upper chamber of the first hydraulic damper (6) below the conduit(s) (31) which open onto the upper part of the upper chamber of the first hydraulic damper (6), in such a manner that the conduit (32) is obstructed entirely (no passage through the conduits 31 and 32) or partially (passage possible through one of the conduits 31) when the knee is in complete extended position in order to ensure that the knee authorizes a dorsiflexion of the ankle in proportion to the movement of the knee during the stance phase and respectively the flexion of the knee results in the dorsiflexion of the ankle during the swing phase. Thus, the oil in the connecting the ankle damper (7) to the knee damper (6) arrives at the top of the knee damper and perpendicularly to the piston of the knee in such a manner that the pressuring of the lower chamber of the ankle damper (7) does not result in the movement of the knee when it is completely extended.

Now, we shall explain the functioning of the variant of execution of the prosthesis in accordance with the invention with reference to FIGS. 7A to 7F.

Figure 7A:
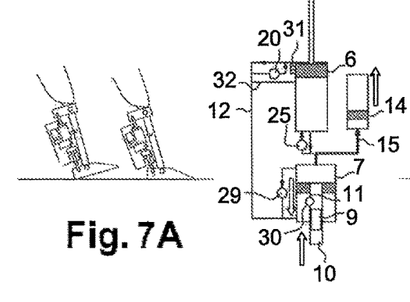
FIGS. 7A to 7F are schematic representations of the variant of execution of the hydraulic system of the prosthesis in compliance with the invention, respectively during the heel strike and the flat placement of the foot on the floor (A), when the tibia returns to the vertical position (B), during the propulsion (C), during the initiation of the flexion of the knee (D), during the flexion of the knee in the swing phase (E) and during the return to extension of the knee (F)

With reference to FIG. 7A, during plantiflexion, i.e., from 0 to 12% of the walking cycle represented in FIG. 3, the support on the heel causes the ankle piston to move upwards. The oil from the upper chamber of the damper (7) of the ankle passes into the lower chamber via the plantiflexion regulation, i.e., the solenoid valve (29). The extra oil is sent towards the collector.

The oil from the lower chamber of the foot arrives perpendicularly to the knee piston. Increasing the pressure thus does not result in the movement of the knee. On the other hand, if the person exerts a flexion torque on the knee, this movement is possible (stanceflex) and is regulated by the regulation of the flexion of the knee, i.e., by the solenoid valve (25) (significant resistance).

Figure 7B:
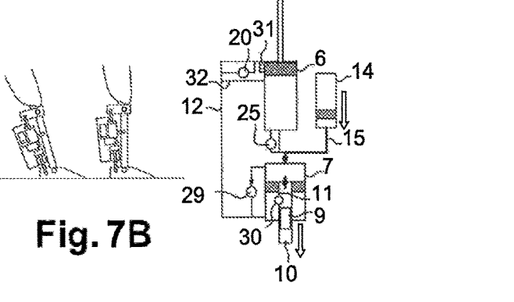

With reference to FIG. 7B, when the tibia is returning to vertical position, i.e., from 12 to 30% of the walking cycle represented on FIG. 3, once the foot is completely placed flat on the ground, the tibia returns to vertical position. The ankle returns to neutral position. The piston of the ankle is lowered. The oil passes from the lower chamber to the upper chamber through the regulation of the dorsiflexion, i.e., through the solenoid valve (30) (until the openings are obstructed by the slide valve (9). The ankle is in neutral position.

Figure 7C:
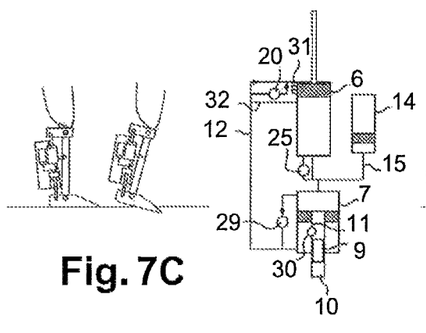

With reference to FIG. 7C, at the time of forward propulsion, i.e., from 30 to 48% of the walking cycle (end of the single foot support) represented on FIG. 3, once the tibia returns to vertical position, the ankle is locked in dorsiflexion (through the extended position of the knee), which allows deforming the foot of the blade to store energy. Return to complete extension of the knee prevents the passage of the oil originating from the lower chamber of the ankle damper (7).

Figure 7D:
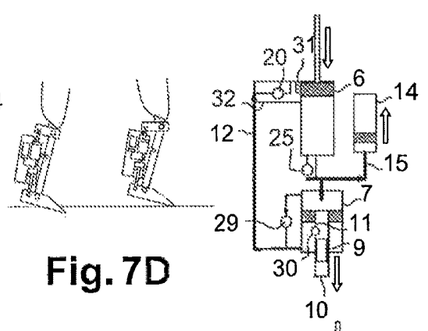

With reference to FIG. 7D, at the time of initiation of the knee flexion, i.e., from 48 to 60% of the walking cycle (second double foot support) represented on FIG. 3, the initiation of the knee flexion is then facilitated. The oil passes from the lower chamber of the damper (6) of the knee to the upper chamber and is regulated by the flexion regulation, i.e., by the solenoid valve (25) (low resistance). The flexion of the knee immediately causes the dorsiflexion of the ankle.

Figure 7E:
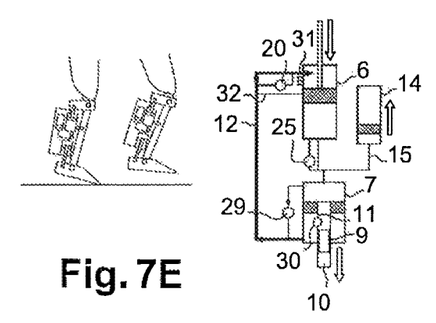

With reference to FIG. 7E, during the flexion in the swing phase, i.e., from 60 to 80% of the walking cycle represented on FIG. 3, the flexion of the knee between 30° and 60° results in the automatic dorsiflexion of the ankle with a ratio of 1/3, i.e., 10° of the ankle dorsiflexion. The ratio of 1/3 is preferred but may be between 1/4 and 2/5. The flexion regulation, i.e., the solenoid valve (25) is controlled electrically in order to be subject to the walking speed or the weight of the prosthesis (inertia of the part below the knee).

Figure 7F:
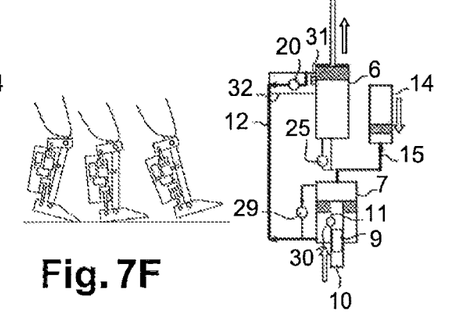

With reference to FIG. 7F, when the knee is returning to extended position in the swing phase, i.e., from 80 to 100% of the walking cycle represented on FIG. 3, once maximum flexion is reached, the knee returns to extended position. Based on the maximum flexion information, the instructions are provided by the microprocessor to block the flexion of the knee in case the person stumbles. The knee piston must be raised rapidly. This extension movement is regulated by the extension valve. This facilitates the passage of the fluid till approximately 5° flexion is achieved. The valve will then gradually close to dampen the terminal impact, i.e., the return of the knee to complete extended position.

Figure 8:
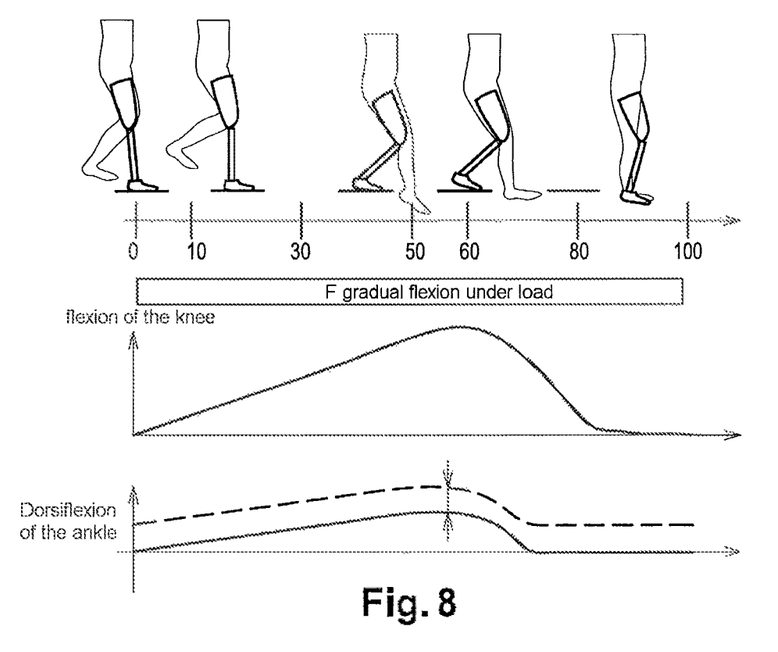
FIG. 8 is a graphical representation of the change in the angles of the knee and ankle when descending stairs.

With reference to FIG. 8, by coupling the knee and ankle, the flexion of the knee while descending the staircase will automatically authorize a gradual dorsiflexion of the ankle. This allows the amputee to normally place his/her foot flat on the stairs and to roll on the big toes only at the end of the support phase. The "ideal" coupling between the knee and the ankle is between 1/4 and 2/5 and preferably 1/3. This means that 60° of the flexion of the knee will result in 20° of dorsiflexion of the ankle. This coupling may be lower (1/4) to adapt to situations. In this case, or to adapt to very rigid stairs, the dorsiflexion stopper may be moved to increase the dorsiflexion of the ankle (adaptation represented with the dotted arrow). The movement of both articulations is controlled by the flexion resistance of the knee, i.e., through a solenoid valve (25).

Figure 9:
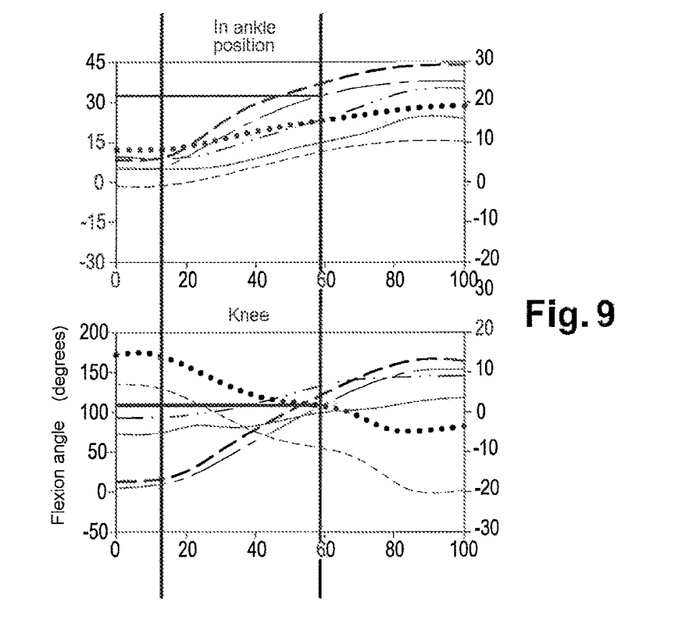
FIG. 9 is a graphical representation of the torque between the angles of the knee and ankle of the femoral knee-ankle prosthesis in compliance with the invention, in stance phase.

With reference to FIG. 9, which is adapted from the publication "Hip, knee, and ankle kinematics of high range of motion activities of daily living. Hemmerich A, Brown H, Smith S, Marthandam S S, Wyss U P. J Orthop Res. 2006 April; 24(4):770-81", the coupling between the angles of the knee and the ankle in the stance phase is particularly useful during triple flexion movements called "squatting". This corresponds especially with the movement for gathering objects from the floor or getting into crouching position. Controlling the flexion of the knee allows significant mobility and control over the knee and the ankle that increases both, static and dynamic stability. This coupling allows ensuring that the flexion of the lower limbs is systematic and thus allows crouching with the back straight. The compensations are limited. The dorsiflexion of the ankle is proportional to the angle of the knee, and the amplitude of the dorsiflexion is 1/3 of the flexion of the knee, i.e., 33° for a knee flexion movement of 100° (from standing to crouching). The ratio of 1/3 is preferred but may be between 1/4 and 2/5. This movement is easily controlled by the person fitted with the device because the knee and ankle are coupled. The person does not control the knee and the ankle separately but controls the combined movement of both articulations using the flexion extension from the hip of the remaining limb.

Figure 10:
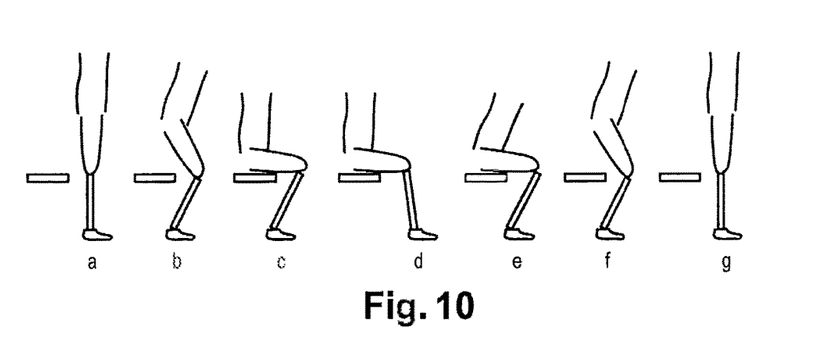
FIG. 10 is a schematic representation of the passage from standing position to seated position (a to d) and from seated position to standing position (d to g)

With reference to FIG. 10, while passing from standing to seated position, the flexion of the knee is controlled by the flexion resistance and the flexion of the knee results in the dorsiflexion of the ankle, which allows maintaining the center of gravity of the person in front of the ankle and behind the knee (b). This allows a stable and secure transition into seated position (c). Once in seated position, only the spring of the collector (14) and the dorsiflexion resistance, via the solenoid valve (29), oppose the plantiflexion of the ankle. The movement is thus made possible, which allows a comfortable seated position (d). To stand up again, it suffices to drag the foot back (with the hand or the other leg), the ankle is in dorsiflexion proportionally to the angle of the knee (e), and the passage into standing position is executed through a coordinated extension of the lower limb. This movement is produced by an extension torque from the hip that lowers as the center of gravity moves closer to the articulation of the hip (e to g). If the chair rise is detected, it is important to adjust the flexion resistance of the knee, i.e., the solenoid valve (25), to the maximum, in order to avoid the person from tipping over backwards.

Figure 11:
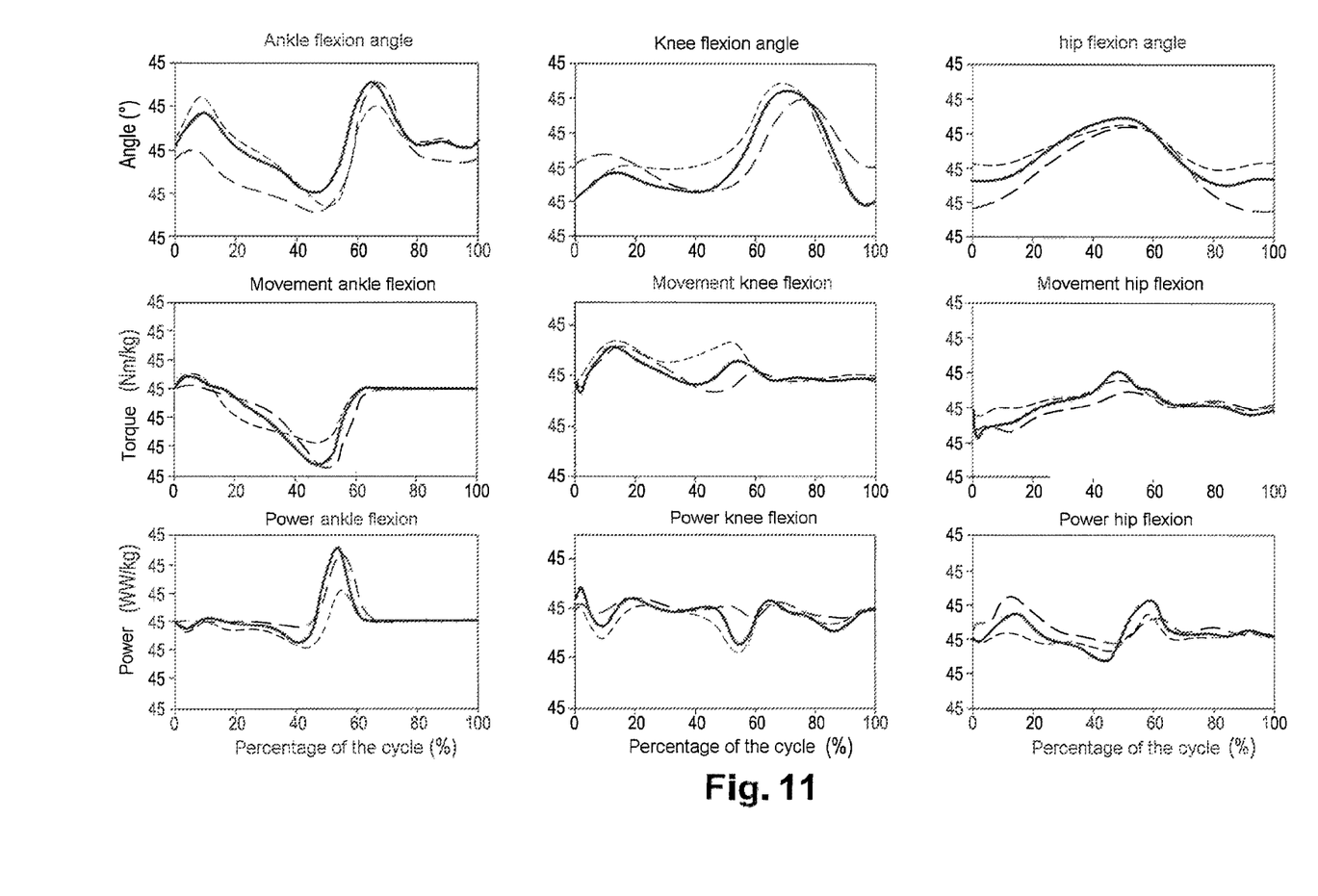
FIG. 11 is a graphical representation as per the percentage of the walking cycle (%) of the angle (expressed in °), of the torque (expressed in N·m/kg) and power (expressed in W/kg) of the ankle, knee and hip for healthy subjects when walking on flat surfaces (underline), descending a 12% slope (dotted line) and when climbing a 12% slope (dashes)

With reference to FIG. 11, while descending a slope, the amplitude of plantiflexion of the ankle is maximum. Between 0 and 12%, the amplitude of plantiflexion is increased, and this happens owing to the plantiflexion resistance that can be adjusted when a slope is detected. The amplitude required for placing the foot flat on the floor is increased while descending a slope. Between 12 and 48% the knee flexes under a controlled load by the flexion resistance, i.e., through a solenoid valve (25). The flexion resistance of the knee, i.e., the solenoid valve (25), during the stance phase can be adapted to the value of the slope in order to increase the resistance during steep slopes and to reduce it on gentle slopes. At the end of single foot support (approximately 48%), the microcontroller must be instructed to switch to swing phase. It may be observed that unlike situations involving walking on flat surfaces, the knee is not completely extended and that the movement of the ankle is reduced. This highlights the fact that when a descending slope is detected, the conditions of transition of the system between the stance and swing phase must be modified.

When descending a slope, it may be useful to modify the dorsiflexion stopper depending on the angle of the slope in order to allow greater stability in case the person stops on this slope by adapting the position of the slide valve (9). The position of the slide valve (9) only determines the dorsiflexion of the ankle if the knee is extended. Thus, the flexion of the knee in support phase authorizes an automatic dorsiflexion of the ankle, reproducing the adaptation in healthy subjects (i.e., increase in dorsiflexion during the support phase).

When climbing a slope, the dorsiflexion stopper is increased depending on the slope by adapting the position of the slide valve (9). This allows significant dorsiflexion from the beginning of the single foot support. The flexion resistance of the knee, via the solenoid valve (25) is set to maximum and must allow putting load on a bowed knee. It may be observed in the healthy subject that only the hip exerts force at the beginning of the support phase (positive strength). This effort of the hip allows completely extending the knee without any internal positive strength of the knee. In case the person stops, the ankle dorsiflexion stopper will be adapted as per the angle of the slope.

The position of the slide valve (9) is modified by the motor, which is not shown in the figures. The motor does not move the ankle but moves the slide valve (9) that defines the dorsiflexion stopper when the knee is extended. The motor is thus used only during changes in slope (or when the user changes footwear), which is economical in terms of energy.

Figure 12:
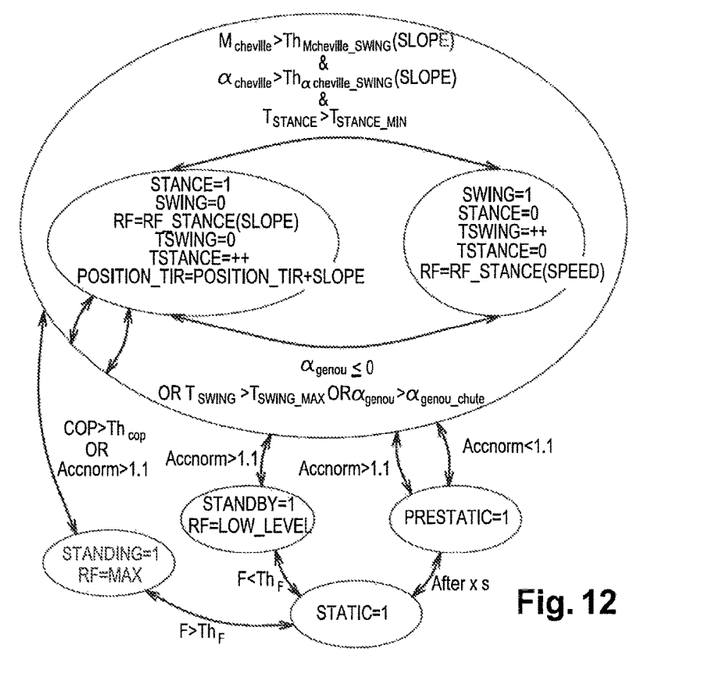
FIG. 12 is a schematic representation in the form of a diagram, of the status and transitions of the control unit depending on the measured and estimated variables.

Now, we shall explain the operating principle of the control unit of the prosthesis in accordance with the invention with reference to FIG. 12.

The kinematic and inertial sensors used are preferably a knee angle sensor, an ankle angle sensor and a bi-axial or tri-axial accelerometer combined with a gyroscope in the sagittal plane that allows measuring the angle of the tibia compared to vertical. Based on these three sensors, it is possible to deduce the angle of the femur and the angle of the foot in comparison with the foot in the sagittal plane.

The used effort sensors are preferably, the effort in the axis of the tibia, the sagittal moment of the ankle and the sagittal moment at another point of the prosthesis. These efforts and moments may be determined favorably by one or several simple measures. For example, the moment of the ankle may be determined by measuring the traction/compression effort along the length of the connecting rod (8), which connects the hydraulic unit to the foot (FIG. 1).

Using these 6 sensors, it is possible to deduce the antero-posterior component and the center of pressure of the effort exerted by the floor on the prosthesis. In the sagittal plane, all the angles and the torsor of effort exerted by the floor on the prosthesis are thus known. Other sensors may be added to allow redundancy and the measurement of in the other spatial planes.

The variables of the algorithm are as follows:

| Variable | Description |
|---|---|
| SLOPE | Estimation of the slope on which the user is walking |
| SPEED | Estimation of the speed at which the user is walking |
| $\alpha_{GENOU}$ | Current value of the knee angle |
| $Th_{\alpha_{GENOU\_SWING(SLOPE)}}$ | Threshold of return to extension of the knee allowing passage into swing phase. This threshold depends on the slope (SLOPE) |
| $M_{CHEVILLE}$ | Current value of the ankle moment |
| $Th_{M_{CHEVILLE\_SWING(SLOPE)}}$ | Threshold of the ankle moment allowing passage into swing phase. This threshold depends on the slope (SLOPE) |
| $T_{STANCE}$ | Duration of the stance phase |
| $T_{STANCE\_MIN}$ | Minimum duration of the stance phase before passage into swing phase |
| RF | Current value of the flexion resistance of the knee (solenoid valve 25). |
| RF_STANCE(SLOPE) | Flexion resistance of the knee in stance phase. This value depends on the slope (SLOPE) |
| RF_SWING(SPEED) | Flexion resistance of the knee in swing phase. This value depends on the walking speed (SPEED) |
| POSITION_TIR | Position of the dorsiflexion stopper slide valve |
| $T_{SWING}$ | Duration of the swing phase |
| $T_{SWING\_MAX}$ | Max duration of the swing phase |
| $\dot{\alpha}_{genou}$ | Current value of the flexion resistance of the knee |
| $\dot{\alpha}_{genou\_chute}$ (SPEED) | Threshold of the knee flexion speed above which the person is considered to be falling. This variable depends on the walking speed (SPEED) |
| Accnorm | Norm of the three components of the accelerometer placed on the tibia |
| F | Effort in the axis of the tibia |
| $Th_F$ | Threshold of the effort on the prosthesis beyond which the prosthesis is considered as being under load. |
| $\dot{COP}$ | Variation of the center of pressure. The center of pressure may be estimated approximately by the ratio between the ankle moment and the effort on the axis of the tibia. |

It is observed that, in this mode of operation, all the sensors are not necessary. The sensors of knee angle measurement, ankle moment and tibia angle as compared to vertical position and effort on the axis of the tibia are sufficient.

With reference to FIG. 12, by default, the system is in STANCE state and the flexion resistance of the knee (RF) is at a high value in order to allow stopping the knee under load (RF_STANCE(SLOPE)). The knee flexion resistance value under load may be modified depending on the slope (SLOPE) on which the person is moving. Similarly, the position of the dorsiflexion stopper POSITION_TIR is adjusted as per the slope (SLOPE). The end of the stance phase is detected when the person is supporting himself on the front part of the prosthetic foot. This translates into a significant dorsiflexion movement of the ankle $M_{CHEVILLE}$ A threshold is $Th_{M_{CHEVILLE\_SWING(SLOPE)}}$ ajusted by the orthoprosthesist depending on the weight and walking style of the amputee. This slope may be modified by the controller depending on the slope.(SLOPE) At the end of the support phase, the knee is near complete extended position. $\alpha_{GENOU}$ $Th_{\alpha_{GENOU\_SWING(SLOPE)}}$ This knee extension threshold may also be modified by the controller depending on the slope. In order to avoid passing into swing phase while standing in support phase, a minimum time for the support phase is required ($T_{STANCE} > T_{STANCE\_MIN}$). These three conditions allow passing into SWING phase.

During the SWING phase, the flexion resistance of the knee is at the value RF_SWING(SPEED). This level of flexion resistance allows the flexion of the knee in swing phase. This value is modified depending on the walking speed of the amputee.

The system returns to STANCE phase if one of the following 4 conditions occur:

$\alpha_{genou}\dot{}<0$, i.e., the knee has reached maximum flexion and has returned to extension. The RF value no longer applies in the movement of the knee. RF is thus set to R_F STANCE to prepare for the next support phase $T_{SWING}>T_{SWING\_MAX}$ The duration of the SWING phase is too long.

$\alpha_{genou}\dot{}>\alpha_{genou\_chute}\dot{}$, the knee flexion speed is higher than the flexion speed reached depending on the walking speed of the person, and there is a risk of falling.

$F>Th_F$: An effort is detected in the axis of the prosthesis.

Alternatively, the condition $\alpha_{genou}\dot{}<0$ may be substituted by the condition $\alpha_{tibia}\dot{}<0$ using the gyroscope fitted on the tibia or on a hydraulic unit for example.

If the norm of the components of the accelerometer is lower than 1.1 g, this means that the tibia is not moving. In addition, by controlling the angle of the knee and ankle it is possible to verify that the entire prosthetic limb is immobile. The prosthetic is thus in a PRE STATIC state. If this state continues for a certain time, it goes into the STATIC state. If there is no effort on the prosthesis (F), it goes directly into STANDBY state and the flexion resistance can be lowered to maximum. Inversely, in case there is effort on the prosthesis, it goes into STANDING state, and the flexion resistance is set to maximum, blocking the flexion of the knee.

Once the norm of the accelerometer components is higher than 1.1 g or if the center of pressure (cop~$M_{CHEVILLE}$/F) varies, the prosthetic returns to STANCE state.

Generally, once movement is detected or if there is a modification of the load on the prosthesis, it goes back to STANCE state.

The walking speed can be estimated based on a very large number of variables measured by the system (support phase time, max knee flexion speed, swing phase time, angular speed of the tibia, etc.).

Figure 13:
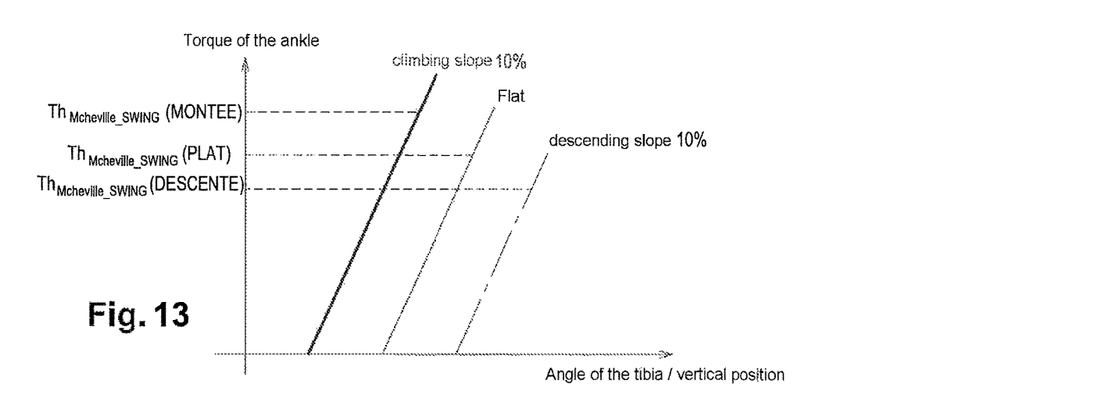
FIG. 13 is a graphical representation, without scale, of the torque of the ankle depending on the angle of the tibia compared to the vertical position when walking on a flat surface, climbing and descending a slope between 30% and 50% during the walking cycle.

FIG. 13 is a graphical representation, without scale, of the torque of the ankle depending on the angle of the tibia compared to the vertical position when walking on a flat surface, climbing and descending a slope between 30% and 50% during the walking cycle. Climbing a slope results in a variation of this curve to the left, and inversely, climbing down a slope results in a variation to the right. The value of this variation is related to the slope on which the user is walking and thus allows determining the SLOPE.

While climbing a slope, the threshold is thus $Th_{M_{CHEVILLE}\_SWING(PLAT)}$ reached earlier in the walking cycle. This threshold $Th_{M_{CHEVILLE}\_SWING(MONTEE)}$ thus be increased in order to delay the passage into swing phase.

Inversely, while climbing down a slope, the threshold is $Th_{M_{CHEVILLE}\_SWING(PLAT)}$ reached later in the walking cycle. The threshold must thus be reduced when climbing down a slope $Th_{M_{CHEVILLE}\_SWING(DESCENTE)}$, in order to facilitate the passage into swing phase.

To obtain the angle of the tibia compared to vertical position, an accelerometer and/or a gyroscope may be used on the tibia or the hydraulic unit.

Finally, it is evident that the abovementioned examples are particular illustrations and are in no case restrictive as regards the domains of application of the invention.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A femoral knee-ankle prosthesis comprising:
a femoral segment suitable for a femoral connection to a user and a tibial segment connected to the femoral segment based on an articulation which reproduces the movements of the knee, the tibial segment being articulated on one foot based on an articulation reproducing the movements of the ankle, a first hydraulic cylinder of which the ends are joined respectively with the femoral and tibial segments, and a second hydraulic cylinder of which the ends are joined respectively with the tibial segment and the foot, an upper chamber of the first hydraulic cylinder is connected to a lower chamber of the second hydraulic cylinder through a conduit connected laterally to the upper chamber of the first hydraulic cylinder, and an electronic control unit that controls both of the first hydraulic cylinder and the second hydraulic cylinder depending on the phase of the walking cycle and a situation faced by the user including a stance phase and a swing phase in such a manner that a first flexion of the knee allows a first dorsiflexion of the ankle in proportion to the movement of the knee during the stance phase and such that a second flexion of the knee results in a second dorsiflexion of the ankle in proportion to the movement of the knee during the swing phase.

2. The femoral knee-ankle prosthesis according to claim 1 wherein the movements of the cylinders are regulated by at least one proportional valve.

3. The femoral knee-ankle prosthesis according to claim 2 wherein the proportional valve is controlled through the electronic control unit depending on the phase of the walking cycle and the situation faced by the user.

4. The femoral knee-ankle prosthesis according to claim 2 wherein the electronic control unit controls the proportional valve in such a manner as to ensure that flexion and dorsiflexion resistances of at least one of the articulation which reproduces the movements of the knee and the articulation which reproduces the movements of the ankle are varied.

5. The femoral knee-ankle prosthesis according to claim 1 wherein the phase of the walking cycle and the situation faced by the user are determined by the electronic control unit based on data obtained from a plurality of sensors placed on at least one of a knee joint of the femoral knee-ankle prosthesis and an ankle joint of the femoral knee-ankle prosthesis.

6. The femoral knee-ankle prosthesis according to claim 5 wherein each sensor consists of a kinetic, kinematic or inertial sensor.

7. The femoral knee-ankle prosthesis according to claim 1 wherein a ratio between the first flexion of the knee and the first dorsiflexion of the ankle is between 1/4 and 2/5.

8. The femoral knee-ankle prosthesis according to claim 7 wherein the ratio between the first flexion of the knee and the first dorsiflexion of the ankle is approximately 1/3.

9. The femoral knee-ankle prosthesis according to claim 1 wherein the electronic control unit comprises at least one microprocessor.

10. The femoral knee-ankle prosthesis according to claim 1 wherein the electronic control unit includes:
an algorithm that determines a moment of at least one of the articulations based on at least one of an angle of a segment adjacent to the respective articulation compared to a reference angle, and an angular speed of the segment adjacent to the respective articulation in a determined reference; and an algorithm that determines controlling instructions for driving means depending on a ratio between a force moment of at least one of the articulations and an angle of a segment adjacent to the respective articulation compared to a reference angle.

11. The femoral knee-ankle prosthesis of claim 1 wherein the upper chamber of the first hydraulic cylinder is hydraulically connected to the lower chamber of the second hydraulic cylinder through the conduit connected laterally to the upper chamber of the first hydraulic cylinder.

12. A femoral knee-ankle prosthesis comprising:
a femoral segment suitable for a femoral connection to a user and a tibial segment connected to the femoral segment based on an articulation which reproduces the movements of the knee, the tibial segment being articulated on one foot based on an articulation reproducing the movements of the ankle, a first hydraulic cylinder of which the ends are joined respectively with the femoral and tibial segments, and a second hydraulic cylinder of which the ends are joined respectively with the tibial segment and the foot, an upper chamber of the first hydraulic cylinder is connected to a lower chamber of the second hydraulic cylinder through a conduit connected laterally to the upper chamber of the first hydraulic cylinder, and an electronic control unit that controls both of the first hydraulic cylinder and the second hydraulic cylinder depending on the phase of the walking cycle and a situation faced by the user including a stance phase and a swing phase in such a manner that a first flexion of the knee allows a first dorsiflexion of the ankle in proportion to the movement of the knee during the stance phase and such that a second flexion of the knee of between 30° and 60° results in a second dorsiflexion of the ankle in proportion to the movement of the knee during the swing phase, wherein a ratio of the second dorsiflexion of the ankle to the second flexion of the knee is between 1/4 and 2/5.

13. The femoral knee-ankle prosthesis of claim 12 wherein the ratio of the second dorsiflexion of the ankle to the second flexion of the knee is 1/3.

14. A method of controlling a femoral knee-ankle prosthesis including a femoral segment suitable for a femoral connection to a user and a tibial segment connected to the femoral segment based on an articulation which reproduces the movements of the knee, the tibial segment being articulated on one foot based on an articulation reproducing the movements of the ankle, a first hydraulic cylinder of which the ends are joined respectively with the femoral and tibial segments, and a second hydraulic cylinder of which the ends are joined respectively with the tibial segment and the foot, an upper chamber of the first hydraulic cylinder is connected to a lower chamber of the second hydraulic cylinder through a conduit connected laterally to the upper chamber of the first hydraulic cylinder, and an electronic control unit that controls both of the first hydraulic cylinder and the second hydraulic cylinder depending on the phase of the walking cycle and a situation faced by the user including a stance phase and a swing phase,
wherein the method comprises a first flexion of the knee allowing a first dorsiflexion of the ankle in proportion to movement of the knee during the stance phase and a second flexion of the knee resulting in a second dorsiflexion of the ankle in proportion to the movement of the knee during the swing phase.

15. The method of claim 14 wherein the second flexion of the knee is of between 30° and 60° and results in the second dorsiflexion of the ankle in proportion to the movement of the knee during the swing phase, wherein a ratio of the second dorsiflexion of the ankle to the second flexion of the knee is between 1/4 and 2/5.

16. The method of claim 15 wherein the ratio of the second dorsiflexion of the ankle to the second flexion of the knee is 1/3.

* * * * *